United States Patent [19]

Sebag et al.

[11] Patent Number: 4,677,232

[45] Date of Patent: Jun. 30, 1987

[54] PROCESS FOR THE PREPARATION OF NONIONIC SURFACE-ACTIVE AGENTS FROM GLYCEROL MONOCHLOROHYDRIN, PRODUCTS OBTAINED AND A COMPOSITION IN WHICH THEY ARE PRESENT

[75] Inventors: Henri Sebag, Paris; Guy Vanlerberghe, Claye-Souilly, both of France

[73] Assignee: L'Oreal, Paris, France

[21] Appl. No.: 808,744

[22] Filed: Dec. 13, 1985

[30] Foreign Application Priority Data

Dec. 17, 1984 [FR] France .............................. 84 19267

[51] Int. Cl.$^4$ ............................................ C07C 41/01
[52] U.S. Cl. .................................... 568/619; 568/608; 568/679; 568/680; 568/616; 424/47; 424/63; 424/70; 514/772
[58] Field of Search ............... 568/679, 608, 680, 619, 568/616

[56] References Cited

U.S. PATENT DOCUMENTS

| 2,520,670 | 8/1950 | Wittcoff et al. | 568/679 |
| 2,520,671 | 8/1950 | Wittcoff et al. | 568/679 |
| 3,431,308 | 3/1969 | Zimmermann et al. | 568/679 |
| 4,105,580 | 8/1978 | Sebag et al. | 568/608 |

FOREIGN PATENT DOCUMENTS

| 522650 | 6/1940 | United Kingdom . |
| 1271519 | 4/1972 | United Kingdom . |

*Primary Examiner*—Howard T. Mars
*Attorney, Agent, or Firm*—Cushman, Darby & Cushman

[57] ABSTRACT

Process for the preparation of water-soluble or water-dispersible polyglycerolated nonionic surface-active agents.

This process is characterized by the polyaddition of glycerol chlorohydrin and of a strong base, and preferably sodium or potassium hydroxide in an aqueous solution, to a (poly)hydroxylated compound.

This process has the advantage of replacing glycidol, which is usually employed, by glycerol chlorohydrin, which is less costly, easier to store than glycidol, and also of avoiding the flash distillation of a flammable volatile solvent.

14 Claims, No Drawings

PROCESS FOR THE PREPARATION OF NONIONIC SURFACE-ACTIVE AGENTS FROM GLYCEROL MONOCHLOROHYDRIN, PRODUCTS OBTAINED AND A COMPOSITION IN WHICH THEY ARE PRESENT

The present invention relates to a new process for the preparation of polyglycerolated nonionic surface-active agents from glycerol monochlorohydrin and from certain organic compounds containing at least one active hydrogen atom, in the presence of a strong base.

"Polyglycerolated" nonionic surface-active agents are already known.

French Pat. No. 2,091,516, or U.S. Pat. No. 3,821,372, describes the preparation of nonionic surface-active agents by a polyaddition of glycidol to alkanediols or to alkyl mercaptans, with alkaline catalysis. This process uses isolated and purified glycidol, a costly raw material, which is difficult to obtain on an industrial scale. In addition, its instability in the presence of some impurities calls for major precautions when it is stored.

French Pat. No. 2,328,764, or U.S. Pat. No. 4,105,580 of the Applicant describes a process for the preparation of nonionic surface-active agents from "crude" glycidol as produced by the dehydrochlorination reaction of glycerol monochlorohydrin by means of a strong base in the presence of a solvent.

Since the starting material employed in the latter process is glycerol monochlorohydrin, a raw material which is less costly than glycidol, this makes it possible to reduce the cost of the products obtained and to limit the hazards of use, by avoiding prolonged storage of glycidol.

Nevertheless, this process calls for the synthesis of glycidol and for the storage of the resultant mixture until it is used.

Furthermore, the addition process for the preparation of nonionic surface-active agents involves the introduction of the isopropanol solution of crude glycidol into the reactor at approximately 150° C. and progressive removal of the solvent by a flash distillation. Such a flash distillation of a flammable volatile solvent presents a hazard which it is better to avoid in a production shop.

The present invention enables these disadvantages to be avoided by the direct use of glycerol monochlorohydrin as a starting material for the preparation of nonionic surface-active agents, without an intermediate synthesis of glycidol and without a flash distillation operation.

The process according to the invention enables nonionic surface-active agents to be prepared from mono- or polyhydroxylated organic compounds by (poly)addition of glycerol monochlorohydrin and of a strong base to these compounds, while water is removed, as the reaction progresses, by distillation.

The process according to the invention comprises the simultaneous addition, at approximately 150° C., of a concentrated solution of an alkali metal hydroxide such as sodium or potassium hydroxide and of glycerol monochlorohydrin to an aliphatic or alkylaryl compound, or a mixture of such compounds (called compound(s) (I) hereinafter), containing one or more alcohol groups, while water is removed by distillation as the reaction progresses.

For a compound (I) containing i hydroxyl groups, the reaction equation can be written diagrammatically:

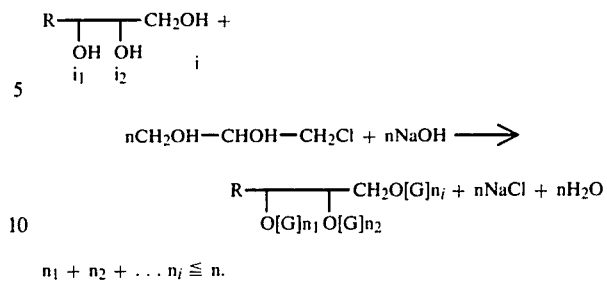

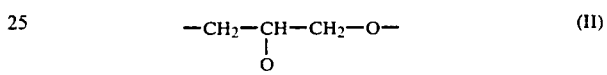

$n_1 + n_2 + \ldots n_i \leq n$.

Each of the symbols $n_1, n_2 \ldots n_i$ denotes the number of hydrophilic moieties G per hydroxyl group; n being the number of moles of glycerol chlorohydrin used per mole of compound (I).

Glycerol monochlorohydrin can undergo hydrolysis or partial polymerization, which explains why the total $n_1 + n_2 + \ldots n_i$ of the hydrophilic groups G which are fixed per mole of compound (I) can be less than n.

G denotes a hydrophilic moiety derived from glycerol:

$$-CH_2-CH-CH_2-O- \quad (II)$$
$$\phantom{-CH_2-}|\phantom{-CH-CH_2-O-}$$
$$\phantom{-CH_2-CH-}O$$

each of the oxygen atoms being capable of being bonded to a hydrogen atom forming part of the moiety G or to the methylene group of another moiety G.

The compounds (I) which can be used within the concept of the invention are:

(a), 1,2-alkanediols containing from 8 to 20, and preferably from 10 to 18, carbon atoms;

(b) (poly)glycerol alkyl ($C_8$–$C_{22}$) ethers, (poly)glycerol alkyl($C_8$–$C_{12}$)aryl ethers, especially (poly)glycerol alkyl($C_8$–$C_{12}$)phenyl ethers, and (poly)glyercol alkenyl($C_8$–$C_{22}$)ethers, containing an average number of hydroxypropylene ether groups which is between 1 and 10, and prepared as described in French Pat. Nos. 1,477,048, 2,027,585 and 2,091,516 or U.S. Pat. Nos. 3,578,719, 3,840,606 and 3,928,224; the preferred (poly)glycerol ethers are those containing from 10 to 18 carbon atoms in the hydrocarbon chain (lipophilic part) and from 0.5 to 4 and advantageously 1 to 4 hydroxypropylene ether groups;

(c) poly(ethylene glycol)alkyl ethers or alkenyl ethers containing from 10 to 18 carbon atoms in the hydrocarbon chain and 2 to 20 oxyethylene moieties.

The actual number i of hydroxyl groups per mole of product (I) can be from 1 to 10.

The symbol n which denotes the number of moles of glycerol chlorohydrin per mole of product (I) can vary from 0.5 to 10, advantageously from 1 to 10, and preferably from 1 to 6.

The reaction may be carried out by a simultaneous introduction, via two different tubing lines, on the one hand, of an aqueous solution of an alkali metal hydroxide, especially sodium hydroxide or potassium hydroxide and, on the other hand, of glycerol monochlorohydrin, at a temperature of 150°–160° C., under an inert atmosphere and preferably under a nitrogen atmosphere, the reaction medium containing a slight excess of alkali metal hydroxide relative to glycerol chlorohydrin.

The alkali metal hydroxide is preferably added in the form of an aqueous solution containing 50 to 60% of water, the water being removed by distillation as the reaction progresses.

The quantity of alkali metal hydroxide used corresponds to the stoichiometric quantity relative to glycerol monochlorohydrin, increased by a 5 to 10% molar excess relative to the (poly)hydroxylated compound (I) employed, this excess acting as a catalyst.

The alkali metal chloride, formed in a molar quantity which is equivalent to the quantity of glycerol monochlorohydrin used, precipitates in the reaction medium during the reaction. The medium will be more or less thick, depending on the structure of the product (I) and the number of moles n of glycerol chlorohydrin which are employed per mole of product (I).

When the value of n is low, the reaction is carried out in a single step.

When the value of n is relatively high, it may be preferable to operate in two steps, that is to say to add a fraction of the scheduled glycerol monochlorohydrin and alkali metal hydroxide, to remove the salt formed, either by filtration or by washing with water, in the presence of a solvent if appropriate, to dry and then to continue the reaction.

An alcohol such as isopropanol or butanol can advantageously be used as a solvent.

When the reaction has ended, the reaction mass is optionally taken up in a solvent to filter off the salt, and then the solvent is removed by distillation. Among the solvents which can be used for this purpose, a hydroxylated solvent may be chosen, such as the lower $C_1$–$C_4$ alcohols, and especially methanol or isopropanol, or a nonpolar solvent, such as toluene.

In some cases it may be advantageous to finish with a high-vacuum evaporation, to partly remove the unreacted starting material I.

The process according to the invention is especially advantageous for the preparation of nonionic surface-active agents having good foaming capacity and containing hydrocarbon chains containing from 10 to 14 carbon atoms, or for the preparation of surface-active agents used as emulsifiers.

Another subject of the invention is the products obtained according to the process described above.

The surface-active agents obtained in this manner can be dissolved or dispersed in water and are suitable for use in cosmetic compositions, especially as foaming, emulsifying or dispersing agents.

Another subject of the invention is the use of the nonionic surface-active agents prepared in this manner in cosmetic compositions.

In the cosmetic compositions, these surface-active agents can be combined with other nonionic, anionic, cationic, zwitterionic or amphoteric surface-active agents, with natural or synthetic polymers, with oils, with waxes, with natural or synthetic thickeners, with solvents, especially water, with alcohols containing 1 to 4 carbon atoms, with the ethers formed by these alcohols with ethylene glycol or propylene glycol, with moistening agents, with active substances, with sunscreens, with preserving agents, with colorants, with pigments, with inorganic salts, with acids, with bases, and with other adjuvants usually employed in cosmetic compositions.

These cosmetic compositions are in the form of a more or less thickened liquid, gel, stick, or emulsion, and can be packaged as an aerosol. They can consist of shampoos, products for use in the shower or bath, products for skin care and treatment, and make-up products.

The invention will be understood better with the help of the following examples, which do not imply any limitation.

EXAMPLE 1

0.5 g of a 40% strength aqueous solution of NaOH is added to 20.2 g (0.1 mole) of 1,2-dodecanediol, and then, at 150° C. and under a gentle stream of nitrogen, 35 g of a 40% strength solution of NaOH, on the one hand, and 38.7 g (0.35 mole) of glycerol monochlorohydrin, on the other hand, are added simultaneously over a period of 2 hours, water being removed as the addition progresses. After being heated at 150° C. for another 30 minutes, the mixture is taken up with 50 ml of isopropanol, and the sodium chloride formed is separated off by filtration. After removal of the solvent by heating under reduced pressure, the product obtained is perfectly soluble in water and has a cloud point of 74° C. in a 10% strength aqueous solution of NaCl.

EXAMPLE 2

5 g of a 40% strength aqueous solution of NaOH are added to 148.4 g (0.5 mole) of polyglycerol decyl ether, prepared from decyl alcohol and epichlorohydrin in proportions of 1/1.5 by the process described in French Pat. No. 1,477,048 and in U.S. Pat. No. 3,578,719, and then, at 150° C., under a gentle stream of nitrogen, 111.6 g (1.125 mole) of NaOH in the form of a 40% strength solution and 124.3 g (1.125 mole) of glycerol monochlorohydrin are simultaneously over a period of 1 hour. When the additions are complete, the reaction mixture is left stirred for another 10 minutes at 150° C. It is then taken up with 120 ml of isopropanol, neutralized with 6.1 ml of 6N HCl, and then filtered. The solvents are removed by heating under reduced pressure. In this way a product is obtained, which is perfectly soluble in water, and has a cloud point of 60° C. in a 25% strength aqueous solution of NaCl.

EXAMPLE 3

3.55 g of a 40% strength aqueous solution of NaOH are added to 141.4 g (0.7 mole) of 1,2-dodecanediol and then, at 150° C., under a stream of nitrogen, 177.5 g of a 40% strength aqueous solution of NaOH, on the one hand, and 193.4 g (1.75 mole) of glycerol monochlorohydrin, on the other hand, are added simultaneously over a period of 2 hours, while water is removed. When the additions are complete, the product is stirred for another 10 minutes at 150° C. After cooling, the reaction mass is taken up with 150 ml of isopropanol and the sodium chloride formed is removed by filtration. Isopropanol is then removed by heating under reduced pressure. 243 g of a residual mass are thus obtained. 50 g of unreacted 1,2-dodecanediol are removed by heating at 180° C. at a pressure of 0.0133–0.066 mbar (0.01–0.05 mm Hg). A product which is perfectly soluble in water is thus obtained. The cloud point is 77° C. in water containing 10% NaCl, and 39° C. in a 25% strength aqueous solution of NaCl.

EXAMPLE 4

72 g of an aqueous solution of NaOH at a concentration of 9.43 meq/g (0.68 mole), on the one hand, and 73 g of glycerol monochlorhydrin (0.66 mole), on the other hand, are added simultaneously over a period of 2 hours, under a stream of nitrogen, to 66.4 g (0.2 mole) of a mixture of poly(ethylene)glycol dodecyl and tetradecyl ethers (containing 3 moles of ethylene oxide), heated to 150° C. while water is removed.

The reaction mass is taken up with isopropanol. After filtration and evaporation of the solvent, 105 g of a product which dissolves in water leaving very slight turbidity are obtained.

After removal of 15 g of volatile material at 210° C. under reduced pressure, a product is obtained which is perfectly soluble in water and whose cloud point is 32° C. in a 25% strength aqueous solution of NaCl.

EXAMPLE 5

79.0 g (0.77 mole) of an aqueous solution of NaOH at a concentration of 9.75 meq/g, on the one hand, and 82.8 g (0.75 mole) of glycerol monochlorohydrin, on the other hand, are added simultaneously at 150° C., over a period of 2 hours, to 73.5 g (0.25 mole) of glycerol nonylphenyl ether. After additional stirring for 15 minutes at 150° C., the reaction mass is left to cool and is taken up with 170 g of isopropanol, and the sodium chloride formed is filtered off. After the solvent has been removed under reduced pressure, 126 g of an amber-coloured product, which is soluble in water with slight turbidity, are recovered.

EXAMPLE 6

62.4 g of a 40% strength aqueous solution of NaOH (0.62 mole) and 66.3 g of glycerol monochlorohydrin (0.6 mole) are added simultaneously under a nitrogen atmosphere at 15° C. to 77.6 g (0.2 mole) of polyglycerol oleyl ether prepared from oleyl alchohol and epichlorohydrin in molar proportions of 1:2, according to French Patent No. 1,477,048.

The addition takes: 1 h 30 minutes.

After cooling, the reaction mass is taken up in 100 g of isopropanol. Sodium chloride is filtered off and rinsed, and then the solvent is removed under reduced pressure.

The residual mass is in the form of a soft, transparent, amber-coloured paste which is soluble in water with opalescence and thickening.

The cloud point, measured at 5% concentration, in a 25% strength aqueous solution of butyl diglycol is above 100° C.

EXAMPLE 7

63 g of sodium hydroxide at a concentration of 9.77 meq/g (0.615 mole) and 66.3 g of glycerol chlorohydrin (0.6 mole) are added simultaneously at 155° C. under a stream of nitrogen, to 85.8 g (0.3 mole) of 1,2-octadecanediol, while water is distilled off as the addition proceeds; the addition takes 2 hours 10 minutes.

Heating and stirring are continued for another 15 minutes. After cooling, the reaction mass is taken up with 250 ml of isopropanol. Sodium chloride is separated off by filtration and the solvent is evaporated off under reduced pressure.

In this way 127 g of product which forms a light-beige-coloured, hard wax when cold, are obtained.

Cloud point in diethylene glycol butyl ether: 95° C.

EXAMPLE 8

109 g of a solution of a sodium hydroxide at a concentration of 9.77 meq/g and 116 g of glycerol chlorohydrin (1.05 mole) are added simultaneously at 155° C., under a stream of nitrogen, over 3 hours, to 85.8 g (0.3 mole) of 1,2-octadecanediol.

The reaction mass is taken up with 300 ml of isopropanol, sodium chloride is filtered off and the solvent is evaporated off.

In this way, a very hard, non-brittle, light-amber-coloured paste is obtained, which is soluble in water above 50° C.

EXAMPLES OF APPLICATION

EXAMPLE A1

The following shampoo is prepared:

| | |
|---|---|
| Compounds prepared according to Example 1 | 2.0 g A.S. |
| Nonionic surfactant prepared from dodecanediol and glycidol (1/3.5), according to French Patent 2,091,516 | 10.0 g |
| Preserving agent q.s. | |
| NaOH q.s. pH = 6 | |
| Water q.s. | 100.0 g |

A.S. = active substance content.

EXAMPLE A2

The following shampoo is prepared:

| | |
|---|---|
| Compounds prepared according to Example 2 | 0.8 g A.S. |
| Triethanolamine alkyl($C_{12}$-$C_{14}$)sulphate | 10.0 g |
| Preserving agent q.s. | |
| NaOH q.s. pH = 7 | |
| Water q.s. | 100.0 g |

EXAMPLE A3

The following shampoo is prepared:

| | |
|---|---|
| Compounds prepared according to Example 3 | 10.0 g A.S. |
| Amphoteric surfactant called "cocoamphocarboxyglycinate" in the CTFA dictionary (Cosmetic Ingredient Dictionary, published by the Cosmetic Toiletry and Fragrance Association, Washington D.C., U.S.A., 3rd edition) and sold under the name of Miranol C2M by the Miranol company. | 2.0 g |
| Quaternized cellulose sold under the name JR 400 by the Union Carbide Company | 0.25 g |
| Preserving agent q.s. | |
| HCl q.s. pH = 6.6 | |
| Water q.s. | 100.0 g |

EXAMPLE A4

The following after-shampoo composition is prepared:

| | |
|---|---|
| Compounds prepared according to Example 3 | 0.8 g A.S. |
| Mixture of cetyl-stearyl alcohol and of cetyl-stearyl alcohol oxyethylenated with 15 moles of ethylene oxide, sold under the name Sinnowax AO by the Henkel Company | 0.3 g |
| Hydroxyethylcellulose, sold under the name Cellosize QP 4400 H by the Union Carbide Company | 0.3 g |
| Mixture of fatty alcohols and oxyethylenated products | 2.0 g |
| Preserving agent q.s. | |
| HCl q.s. pH = 5.5 | |
| Water q.s. | 100.0 g |

EXAMPLE A5

The following shampoo is prepared:

| | |
|---|---|
| Compounds prepared according to Example 2 | 8.0 g A.S. |
| Sodium and magnesium lauryl ether sulphate at a concentration of 30% AS, sold under the name of Texapon ASV by the Henkel Company | 3 g |
| Quaternary polyvinylpyrrolidone copolymer with a molecular weight of approximately 1,000,000, marketed under the name Gafquat 755 by the General Aniline Company | 0.4 g |
| Preserving agent q.s. | |
| HCl q.s. pH = 6.9 | |
| Water q.s. | 100 g |

EXAMPLE A6

The following shampoo is prepared:

| | |
|---|---|
| Compounds prepared according to Example 2 | 12 g A.S. |
| Hydroxypropylated guar gum, sold under the name Jaguar HP 60 by the Celanese Company | 0.5 g |
| Preserving agent q.s. | |
| Perfumes q.s. | |
| HCl q.s. pH = 5 | |
| Water q.s. | 100.0 g |

EXAMPLE A7

The following shampoo is prepared:

| | |
|---|---|
| Compounds prepared according to Example 3 | 15 g A.S. |
| Preserving agent q.s. | |
| Perfumes q.s. | |
| NaOH q.s. pH = 6.5 | |
| Water q.s. | 100 g |

EXAMPLE A8

The following soft body-cleansing liquid is prepared:

| | |
|---|---|
| Compounds prepared according to Example 3 | 9.0 g A.S. |
| Hydroxyethylcellulose, sold under the name Natrosol 250 by the Hercules Company | 0.3 g |
| Ethylene oxide propylene oxide copolymer, sold under the name Pluronic L 62 by the BASF Wyandotte Company | 5.0 g |
| Preserving agents, perfumes q.s. | |
| Water q.s. | 100 g |

EXAMPLE A9

The following face-cleansing gel is prepared:

| | |
|---|---|
| Compounds prepared according to Example 4 | 1.8 g A.S. |
| Hexylene glycol | 5.0 g |
| Crosslinked acrylic acid polymer, sold under the name Carbopol 940 by the Goodrich Company | 0.75 g |
| Triethanolamine | 0.75 g |
| Preserving agents, perfumes q.s. | |
| Water q.s. | 100 g |

EXAMPLE A10

The following body-exfoliant gel is prepared:

| | |
|---|---|
| Compounds prepared according to Example 1 | 15 g A.S. |
| Propylene glycol | 10 g |
| Crosslinked acrylic acid polymer, sold under the name Carbopol 941 by the Goodrich Company | 0.6 g |
| Triethanolamine | 0.6 g |
| Polyethylene powder | 2 g |
| Preserving agents, perfumes q.s. | |
| Water q.s. | 100 g |

EXAMPLE A11

Waterproof mascara

| | |
|---|---|
| Compound prepared according to Example 7 | 4 g |
| Compound prepared according to Example 8 | 0.1 g |
| Carnauba wax | 5 g |
| Candelilla wax | 5 g |
| Ethyl alcohol | 3 g |
| Montmorillonite modified with an organic substance | 4 g |
| Talc | 10 g |
| Black iron oxide | 10 g |
| Isoparaffin q.s. | 100 g |

EXAMPLE A12

Mascara in the form of a water-in-oil emulsion

| | |
|---|---|
| Compounds prepared according to Example 7 | 2 g |
| Compounds prepared according to Example 8 | 2 g |
| Beeswax | 8 g |
| Paraffin wax | 3 g |
| Triethanolamine stearate | 15 g |
| Methyl para-oxybenzoate | 0.2 g |
| Propyl para-oxybenzoate | 0.2 g |
| Guar gum | 4 g |
| Rosin | 2 g |
| Ozokerite | 10 g |
| Black iron oxide | 5 g |
| Sterile deionized water q.s. | 100 g |

EXAMPLE A13

Anti-bruise stick

| | |
|---|---|
| Compounds prepared according to Example 7 | 1.5 g |
| Compounds prepared according to Example 8 | 1.5 g |
| Candelilla wax | 4 g |
| Microcrystalline wax | 8 g |
| Cocoa butter | 8 g |
| Isopropyl myristate | 44.9 g |
| Talc | 7 g |
| Butylated hydroxytoluene | 0.1 g |
| Iron oxide | 5 g |
| Titanium dioxide | 20 g |

EXAMPLE A14

Cheek rouge

| | |
|---|---|
| Compounds prepared according to Example 7 | 3 g |
| Compounds prepared according to Example 8 | 5 g |
| Stearic acid | 2.5 g |
| Polyethoxylated sorbitan monostearate | 0.5 g |
| Paraffin oil | 10 g |
| Isopropyl myristate | 10 g |
| Triethanolamine | 1 g |
| Sorbitol | 5 g |
| Paraffin wax | 1 g |
| Carnauba wax | 2 g |
| Magnesium silicate | 3 g |
| Red iron oxide | 5 g |

-continued

| | |
|---|---|
| Titanium dioxide | 2 g |
| Titanium mica | 3 g |
| Preserving agent | 0.1 g |
| Water q.s. | 100 g |

We claim:

1. Process for the preparation of water-soluble or water-dispersible (poly)glycerolated nonionic surface-active agents, from (poly)hydroxylated organic compounds used as a starting material, which process is characterized in that glycerol monochlorohydrin and a strong base are added to the said (poly)hydroxylated compound while water is removed by distillation as the reaction proceeds, said strong base being an aqueous solution of sodium hydroxide or of potassium hydroxide.

2. Process according to claim 1, characterized in that the addition of the glycerol monochlorohydrin and the strong base is carried out at a temperature of approximately 150° C.

3. Process according to claim 1, characterized in that the quantity of strong base added corresponds to the stoichiometric quantity relative to glycerol monochlorohydrin, increased by a 5 to 10% molar excess relative to the (poly)hydroxylated compound, the addition being carried out under an inert atmosphere.

4. Process according to claim 1, characterized in that at the end of the reaction the reaction mass is taken up in a solvent, the salt formed is filtered off and the solvent is removed by distillation.

5. Process according to claim 4, characterized in that a lower $C_1$–$C_4$ alcohol or a nonpolar solvent such as toluene is used as the solvent.

6. Process according to claim 1, characterized in that the reaction is carried out in a single step.

7. Process according to claim 1, characterized in that the reaction is carried out in two steps, that is to say a part of the glycerol monochlorohydrin and of the strong base required for the reaction are added, the salt formed is removed by filtration or by washing with water, in the presence of a solvent if appropriate, drying is carried out and then the polyaddition is continued.

8. Process according to claim 7, characterized in that an alcohol such as isopropanol or butanol is used as a solvent to facilitate the washing.

9. Process according to claim 1, characterized in that the reaction is finished by evaporation in high vacuum to partly remove the unreacted (poly)hydroxylated starting materials.

10. Process according to claim 1, characterized in that 0.5 to 10 moles of glycerol monochlorohydrin are added per mole of (poly)hydroxylated starting material.

11. Process according to claim 1, characterized in that the (poly)hydroxylated starting material is chosen from the group consisting of 1,2-alkanediols, (poly)glycerol alkyl ethers, (poly)glycerol alkylaryl ethers, (poly)glycerol alkenyl ethers), poly(ethylene glycol)alkyl ethers and poly(ethylene glycol)alkenyl ethers.

12. Process according to claim 11, characterized in that the 1,2-alkanediols contain from 8 to 20 carbon atoms, in that the (poly)glycerol alkyl ethers, the (poly)glycerol alkylaryl ethers and the (poly)glycerol alkenyl ethers each contain from 8 to 22 carbon atoms in the hydrocarbon chain, and a number of hydroxypropylene ether groups of between 1 and 10, and in that the poly(ethylene glycol)alkyl and alkenyl ethers contain from 10 to 18 carbon atoms in the hydrocarbon chain and from 2 to 20 oxyethylene moieties.

13. Process according to claim 12, characterized in that the (poly)hydroxylated starting material is chosen from the group consisting of 1,2-alkanediols containing from 10 to 18 carbon atoms and (poly)glycerol ethers containing from 10 to 18 carbon atoms in the hydrocarbon chain, and from 0.5 to 4 hydroxypropylene ether groups.

14. Process for the preparation of water-soluble or water-dispensible (poly)glycerolated nonionic surface-active agents from (poly)hydroxylated organic compounds comprising adding glycerol monochlorohydrin and a strong base to said (poly)hydroxylated compound while water is removed by distillation as the reaction proceeds, the amount of said strong base being added corresponding to the stoichiometric amount relative to said glycerol monochlorohydrin, increased by a 5 to 10 percent molar excess relative to said (poly)hydroxylated compound, the addition of said glycerol monochlorohydrin and said strong base being carried out under an inert atmosphere.

* * * * *